US00RE35816E

United States Patent [19]

Schulz

[11] E Patent Number: Re. 35,816

[45] Reissued Date of Patent: Jun. 2, 1998

[54] METHOD AND APPARATUS FOR THREE-DIMENSIONAL NON-CONTACT SHAPE SENSING

[75] Inventor: Waldean A. Schulz, Boulder, Colo.

[73] Assignee: Image Guided Technologies Inc., Boulder, Colo.

[21] Appl. No.: 415,126

[22] Filed: Mar. 30, 1995

Related U.S. Patent Documents

Reissue of:

[64] Patent No.: 5,198,877
Issued: Mar. 30, 1993
Appl. No.: 597,505
Filed: Oct. 15, 1990

[51] Int. Cl.[6] ..... G01B 11/14; G01B 11/24; G01C 3/08

[52] U.S. Cl. ..... 356/376; 356/375; 356/3.14; 356/141.4

[58] Field of Search ..... 356/375, 376, 356/3.14, 141.4, 139.03, 141.5, 152.1; 128/653.1, 653.2; 606/130; 250/559.19, 559.22, 559.23, 559.29, 559.31

[56] References Cited

U.S. PATENT DOCUMENTS

| | | | |
|---|---|---|---|
| 3,821,469 | 6/1974 | Whetstone et al. . | |
| 3,983,474 | 9/1976 | Kuipers . | |
| 4,209,254 | 6/1980 | Reymond et al. | 356/141 |
| 4,585,350 | 4/1986 | Pryor | 356/376 |
| 4,649,504 | 3/1987 | Krouglicof et al. | 356/141 |
| 4,660,970 | 4/1987 | Ferrano . | |
| 4,701,047 | 10/1987 | Eibert et al. . | |
| 4,701,049 | 10/1987 | Beckmann et al. | 356/1 |
| 4,705,395 | 11/1987 | Hageniers . | |
| 4,705,401 | 11/1987 | Addleman et al. . | |
| 4,709,156 | 11/1987 | Stephan et al. . | |
| 4,721,384 | 1/1988 | Dietrich et al. . | |
| 4,721,388 | 1/1988 | Takagi et al. | 356/376 |

(List continued on next page.)

OTHER PUBLICATIONS

A.M. Coblentz, Robin E. Herron, Biostereometrics '85, 3–6 Dec. 1985 Stereometric Measurement System for Quantification of Object Forms, P.Fischer, F.Mesqui, F.Kaeser.

Robert P. Burton, Ivan E. Sutherland, Twinkle Box–A Three Dimensional Computer Input Device, May 6–10, 1974, AFIPS Conference Proceedings vol. 43.

Henry Fuchs, Joe W. Duran, Brian W. Johnson, Zvi. M. kedem, Acquisition & Modeling of Human Body Form Data, SPIE vol. 166, Jul. 1978.

V. Macellari, CoSTEL:a Computer Peripheral Remote Sension Device for 3–Dimensional Monitoring of Human Motion, May, 1983.

F. Mesqui, F.Kaeser, P.Fischer, Real–Time, Noninvasive Recording & Three–Dimensional Display of the Functional Movements of an Arbitrary Mandible Point, SPIE vol. 602 Biostereometrics, Dec. 1985.

Yasuo Yamashita, Three–dimensional Stereometric Measurement System Using Optical Scanners, Cylindrical Lenses, & Line Sensors, SPIE 361, Aug. 1982.

*Primary Examiner*—Hoa Q. Pham
*Attorney, Agent, or Firm*—Michael G. Gilman

[57] ABSTRACT

This method and apparatus optically samples numerous points on the surface of an object to remotely sense its shape utilizing two stages. The first stage employs a moveable non-contact scanner, which in normal operation sweeps a narrow beam of light across the object, illuminating a single point of the object at any given instant in time. The location of that point relative to the scanner is sensed by multiple linear photodetector arrays behind lenses in the scanner. These sense the location by measuring the relative angular parallax of the point. The second stage employs multiple fixed but widely separated photoelectronic sensors, similar to those in the scanner, to detect the locations of several light sources affixed to the scanner, thereby defining the absolute spatial positions and orientations of the scanner. Individual light sources are distinguished by time-multiplexing their on-off states. A coordinate computer calculates the absolute spatial positions where the scanner light beam is incident on the object at a given instant and continuously on a real time basis to generate a computer model of the object.

22 Claims, 5 Drawing Sheets

U.S. PATENT DOCUMENTS 4,733,969 3/1988 Case et al. .
4,737,032 4/1988 Addleman et al. .
4,743,771 5/1988 Sacks et al. .
4,745,290 5/1988 Frankel et al. .
4,753,528 6/1988 Hines et al. .
4,761,072 8/1988 Pryor et al. .
4,764,015 8/1988 Bieringer et al. .
4,764,016 8/1988 Johansson .
4,767,934 8/1988 Stauffer .
4,775,235 10/1988 Hecker et al. .
4,782,239 11/1988 Hirose et al. .
4,794,262 12/1988 Sato et al. .
4,803,645 2/1989 Ohtomo et al. .
4,821,200 4/1989 Oberg .
4,822,163 4/1989 Schmidt .
4,825,091 4/1989 Breyer et al. .
4,829,373 5/1989 Leberl et al. .
4,836,778 6/1989 Baumrind et al. .
4,982,188 1/1991 Fodale et al. ..... 356/141

METHOD AND APPARATUS FOR THREE-DIMENSIONAL NON-CONTACT SHAPE SENSING

Matter enclosed in heavy brackets [ ] appears in the original patent but forms no part of this reissue specification; matter printed in italics indicates the additions made by reissue.

BACKGROUND OF THE INVENTION

1. Field of the Invention

This invention relates to optical mensuration devices in general, and in particular to an improved method and apparatus for the optical mensuration of the surface shape of a three-dimensional object.

2. Brief Description of the Prior Art

Numerous mensuration systems exist in the prior art for sensing the locations of surface points on three-dimensional solid objects in relation to a predefined fixed reference frame or coordinate system for input into an application system, such as a computer or other device for measurement or analysis. For example, one type of mensuration system that can be used to determine the location of a single point on the surface of an object includes the use of a narrow projected beam of light to illuminate a tiny area or spot on the surface of the object. A lens in the system is positioned on an optical axis oblique to the axis of the projected beam and is used to focus the reflected light from the illuminated spot onto a photoelectric sensor or onto a linear array of sensors. Since the optical axis of the lens and sensor assembly in that type of system is not coincident with the axis of the projected beam, the position of the image of the illuminated spot on the sensor will depend on the location of the particular illuminated surface point with respect to the illuminating beam. Therefore, the location of the illuminated point with respect to the predetermined reference frame can be determined by computing the distance of the illuminated surface point from the origin of the light beam which, of course, is known. Examples of such point illumination optical mensuration systems are found in the following U.S. Pat. Nos. 4,660,970; 4,701,049; 4,705,395; 4,709,156; 4,733,969; 4,743,770; 4,753,528; 4,761,072; 4,764,016; 4,782,239; and 4,825,091.

Of course, to determine the overall shape of an object, numerous individual surface points, along with their respective locations, must be measured and recorded. Such optical measurement of multiple surface points of an object is typically accomplished by mounting the beam projector on a moveable scanning head capable of being moved from point-to-point with very high precision, such as the type commonly found on numerically controlled milling machines. By precisely moving the beam projector mounted on the scanning head in a raster-like scanning pattern, it is possible to measure the surface shape of the object being scanned by measuring the individual locations of surface points individually illuminated by the point-like scanning beam as it is scanned over the object's surface. Alternatively, the object itself can be moved while the scanning head remains stationary. One disadvantage of this type of system is that only one side of the object may be scanned at any one time, since other sides of the object are hidden by the side being scanned. Scanning of these hidden sides can only be accomplished by relocating either the scanning head or the object to expos the previously hidden surfaces to the scanning beam. Obviously, such a relocation requires time and precision equipment to keep track of the changed position of the scanning head, or the object in relation to the fixed reference frame so that the new surface data will correspond to the previously obtained surface data. Helical or three-dimensional scanning heads solve this problem by allowing the entire object to be scanned at once. However, such helical systems are relatively expensive, since they require complex mechanical apparatus to move the scanning head around the object in three-dimensions.

Regardless of the scanning method used, however, deep holes, overhangs, undercuts, and surfaces nearly parallel to the axis of the scanning beam reduce the accuracy of the system, since it is difficult to accurately measure these points, if they can even be illuminated by the scanning beam at all. For example, such systems cannot completely scan the inside, outside, and handle details of a coffee cup without requiring the scanning apparatus to be relocated or the object to be reoriented so that the inside surfaces or other surfaces previously hidden from the scanning beam can be illuminated by the beam, thus measured and recorded. As discussed earlier, such re-locations or re-orientations have the disadvantage of having to recalibrate the scanning apparatus, or otherwise recorrelate the new surface points with respect to the original coordinate system. Moreover, even if such relocations or reorientations are not required, such as in the case of a helical scanning apparatus, there is still a severe loss of accuracy when scanning near the top or bottom of a rounded object, unless the scanning head and detector are relocated to better illuminate and detect such points. Furthermore, these types of systems are not very portable or adaptable since they require high precision electro-mechanical or other apparatus to accurately move the scanning heads (or the object) and define their positions in relation to the predetermined reference frames. Therefore, all these prior art scanning systems will usually require some type of relocation of the scanning apparatus or reorientation of the object to completely measure and record all of the surface details.

A variant of the above-described systems projects a thin beam of light in a single plane which, of course, is incident as a line, as opposed to a point, on the surface of the object being scanned. The intersection of this plane of light with the object's surface thus forms a brightly illuminated contour line. A two-dimensional electronic video camera or similar device whose optical axis is not coincident with the axis of the illuminating beam, detects the image of this contour line. Again, since the optical axis of the camera is not coincident with the axis of the illuminating light beam, it views the contour line from an oblique angle, thus allowing location of the contour line to be precisely determined in relation to the known position of the beam projector. Examples of inventions using this type of system are found in the following U.S. Pat. Nos. 4,821,200; 4,701,047; 4,705,401; 4,737,032; 4,745,290; 4,794,262; 4,821,200, 4,743,771; and 4,822,163.

To measure more than one contour line of an object, either the measuring apparatus or the object is panned along (or rotated about) an axis through the object. While these line scanning devices share similar drawbacks with the point scanning devices previously described, they do operate much faster, gathering a larger number of sample points during a given scanning interval. Unfortunately, the accuracy of each surface sample point is limited by the relatively low resolution of the two-dimensional charge coupled device (CCD) sensors found in most video cameras, which is typically in the range of 1 part in 512. Even worse, these systems still suffer the disadvantages of the point scanning systems in that either the scanning head or the object must be relocated or re-oriented to completely and accurately record all of the surface details of an object.

Still other mensuration systems track the positions of specific points in three-dimensional space by using small radiating emitters which move relative to fixed receiving sensors, or vice versa. Such radiation emitters may take the form of sound, light, or nutating magnetic fields. Another mensuration system uses a pair of video cameras plus a computer to calculate the position of homologous points in the pair of stereographic video images. See, for example, U.S. Pat. Nos. 4,836,778 and 4,829,373. The points tracked by this system may be passive reflectors or active light sources. The latter simplifies finding and distinguishing the points.

Additional prior art relevant to this patent application are found in the following references:

Burton, R. P.; Sutherland, I. E.; "Twinkle Box—a three dimensional computer input device", National Computer Conference, AFIPS Proceedings, v 43, 1974, p 513–520;

Fischer, P.; Mesqui, F.; Kaeser, F.; "stereometric measurement system for quantification of object forms", SPIE Biostereometrics 602, 1985, p 52–57;

Fuchs, H.; Duran, J.; Johnson, B.; "Acquisition and Modeling of Human Body Form Data", Proc. SPIE, v 166, 1978, p 94–102;

Macellari, V.; "A Computer Peripheral Remote Sensing Device for 3-Dimensional; Monitoring of Human Motion", Med. & Biol. Eng. & Comput., 21, 1983, p 311–318;

Mesqui, F.; Kaeser, F.; Fischer, P.; "real-time, noninvasive recording and 3-d display of the functional movements of an arbitrary mandible point", SPIE Biostereometrics 602, 1985, p 77–84;

Yamashita Y.; Suzuki, N.; Oshima, M.; "Three-Dimensional Stereometric Measurement System Using Optical Scanners, Cylindrical Lenses, and Line Sensors", Proc. SPIE, v. 361, 1983, p. 67–73.

In particular, the paper by Fuchs, et al. (1978) describes a basic method of tracking a light source in three-dimensional space. The method is based on using three or more one-dimensional sensors, each consisting of a cylindrical lens and a linear array of photodetectors, such as charge coupled devices (CCDs), to determine the location of the currently radiating source.

Numerous other methods have been devised and patented for determining the position of a point along a line, within a plane, or in three-dimensional space. Devices employing these methods include photographic camera rangefinders, tablet digitizers, coordinate measuring machines, and surveying tools. Some exploit sound, magnetic fields, or mechanical apparatus for mensuration, and there are other devices employing x-rays, nuclear magnetic resonance, radar, sonar, and holography to sense the shapes of objects.

Unfortunately, each of the above mensuration systems has its own set of drawbacks, which include high cost, poor accuracy, poor resolutions, awkward or difficult use, limitations on geometrical complexity, excessive numerical computation, or slow measurement speed. Experience has shown that no single prior art system best suits all three-dimensional measurement applications. For example, there is no existing mensuration device that can perform even straightforward anatomical measurements of a person without significant drawbacks.

Thus, there remains a need for a non-contact, three-dimensional optical mensuration system which is capable of accurate, speedy, convenient, and inexpensive sensing of three-dimensional geometric shapes or objects. Ideally, the scanning head of such an improved system should be hand-held to allow the operator to easily move the scanning beam over some of the more complex surface details of the object while dispensing with the need for the expensive, cumbersome, and high precision scanning head positioning apparatus currently required. Such a hand-held scanner must also provide the accuracy and precision associated with currently available optical mensuration systems, that is, it must be able to accurately measure and precisely locate the surface details of the object in relation to the predetermined reference frame.

SUMMARY OF THE INVENTION

Accordingly, it is an object of the present invention to provide an improved, non-contact, three-dimensional optical mensuration system capable of accurately sensing the surface shapes of three-dimensional objects without the numerous drawbacks associated with the prior art systems.

It is another object of this invention to provide an optical mensuration system that is inexpensive, portable, and easy to use.

It is a further object of this invention to provide a three-dimensional optical mensuration system which can quickly scan the surface of the object without the need for expensive, complicated, and high precision mechanical positioning apparatus to position either the scanning head or the object being scanned.

A still further object of this invention is to provide a portable, hand-held, and hand-maneuverable scanner for the three-dimensional, non-contact shape-scanning and/or mensuration of three-dimensional objects.

Additional objects, advantages, and novel features of this invention shall be set forth in part in the description that follows, and in part will become apparent to those skilled in the art upon examination of the following or may be learned by the practice of the invention. The objects and the advantages of the invention may be realized and attained by means of the instrumentalities and in combinations particularly pointed out in the appended claims.

To achieve the foregoing and other objects and in accordance with the purposes of the present invention, as embodied and broadly described herein, the apparatus for three-dimensional, non-contact shape sensing of this invention may comprise a hand held scanning head with a light source for projecting a scanning light beam over the surface of the object being scanned. Two spot detectors mounted on the hand-held scanning head are operative to detect the position of the illuminated spot on the surface of the object in relation to the scanning head. Three pilot light detectors, the positions of which are known with respect to a predetermined coordinate system, detect the positions of the three pilot light emitters positioned in spaced-apart relation on the scanning head as pilot light emitters are strobed in sequence. A coordinate computer connected to the scanning head and to the pilot light detectors receives data from the spot detectors and calculates the position of the illuminated spot with respect to the scanning head. The coordinate computer then calculates the various positions and orientations of the scanning head in relation to the predetermined coordinate system on a real time basis from the data received from the pilot light detectors. Finally, the coordinate computer calculates the position of the illuminated spot in relation to the predetermined coordinate system by correlating the position of the illuminated spot in relation to the scanning head with the position of the scanning head in relation to the predetermined coordinate system.

The method of this invention includes the steps of sweeping a scanning beam projected from the hand held scanning head over the surface of the object being scanned to illuminate a spot on the surface of the object, detecting the position of the illuminated spot with respect to the scanning head, detecting the position of the scanning head in relation to a predetermined coordinate system, and computing the position of the illuminated spot in relation to the predetermined coordinate system by correlating the position of the illuminated spot in relation to the scanning head with the position of the scanning head in relation to the predetermined coordinate system.

BRIEF DESCRIPTION OF THE DRAWINGS

The accompanying drawings, which are incorporated herein and form a part of the specification illustrate preferred embodiments of the present invention, and together with the description, serve to explain the principles of the invention. In the drawings.

DETAILED DESCRIPTION OF THE PREFERRED EMBODIMENT

Figure 1:
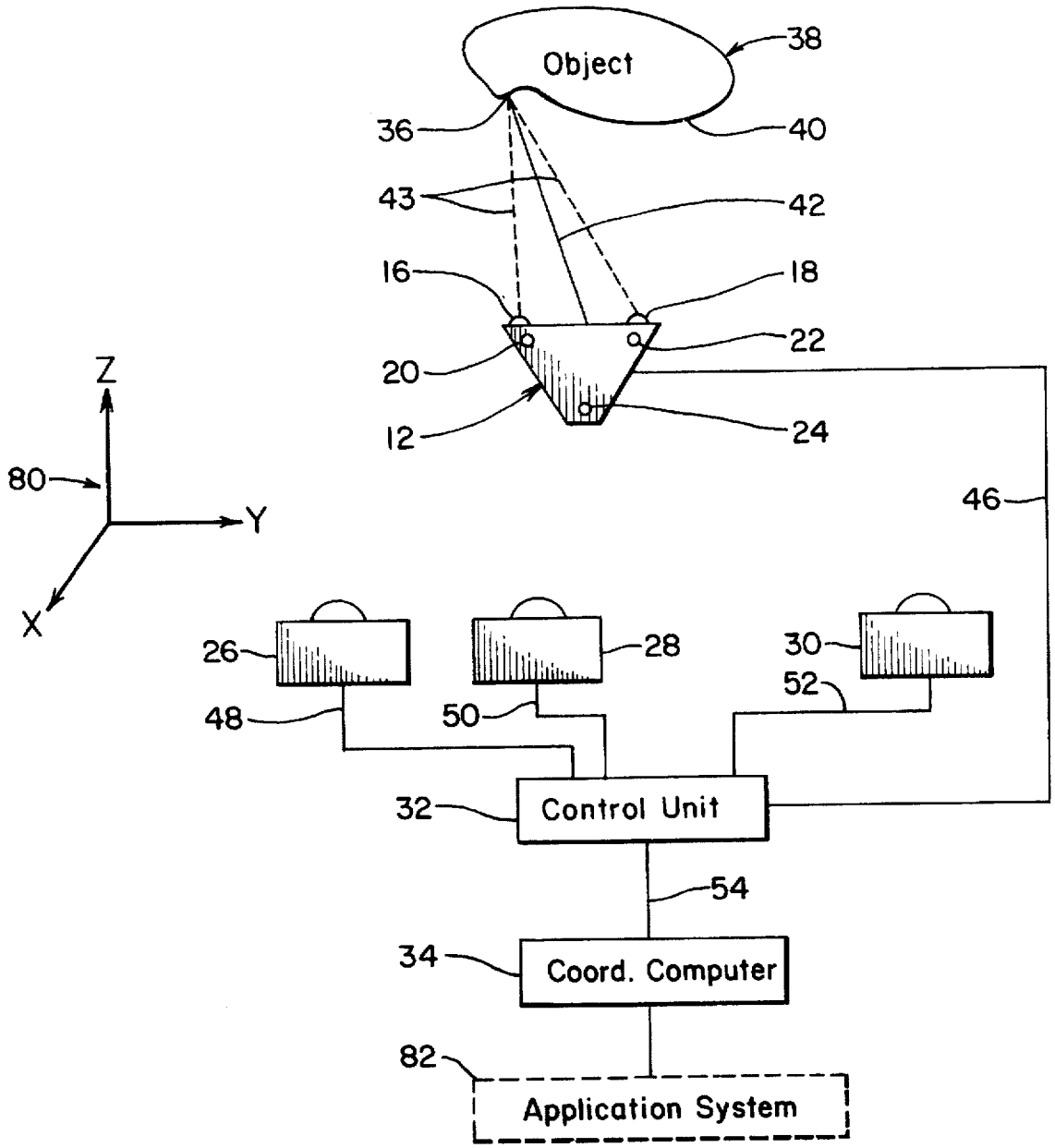
FIG. 1 is a block diagram of the optical mensuration apparatus of the present invention showing the major components.

The optical mensuration apparatus 10 of the present invention is shown schematically in FIG. 1 and comprises a hand-held or moveable scanning head 12 housing light beam projecting apparatus 14 (not shown in FIG. 1, but shown in FIG. 3), two one-dimensional spot sensors or detectors 16, 18, and three pilot light emitters 20, 22, and 24. Three remotely located, one-dimensional pilot light sensors 26, 28, and 30 are mounted in fixed, spaced-apart relation to each other and are located at known positions with respect to a predetermined reference coordinate system or frame 80. These three pilot sensors 26, 28, and 30 sense the light projected by the individual pilot light emitters 20, 22, and 24 and generate electrical output signals from which are derived the location of the scanning head 12 with respect to the fixed coordinate system 80. A control unit 32 connected to the moveable scanning head 12 via data line 46 and connected to the remotely located sensors 26, 28, and 30 via data lines 48, 50, and 52, respectively, synchronizes the time multiplexing of the three pilot emitters 20, 22, and 24, controls the operation of the beam projecting apparatus 14, and receives data from the two spot sensors 16, 18 on scanning head 12, as will be completely described below. A coordinate computer 34, connected to control unit 32 by data line 54 calculates the three-dimensional spatial coordinates of the illuminated spot 36 in relation to the predetermined coordinate reference frame 80, which position information can then be used by an application system 82.

In operation, the light beam projecting apparatus 14 housed in the hand held scanner head 12 directs a narrow beam of light or scanning beam 42 onto the surface 40 of object 38 to illuminate a small portion or spot 36 on the surface 40. Reflected light 43 from illuminated spot 36 is detected by the two one-dimensional spot sensors or detectors 16, 18 mounted on scanner head 12. These sensors 16, 18 sense the location of the illuminated spot 36 with respect to the position of the moveable scanner 12 by measuring the relative angular parallax of the reflected light 43 from illuminates spot 36. Next, the spatial position and orientation of the moveable scanner head 12 at that same instant are determined by measuring the locations of the three time multiplexed pilot light emitters 20, 22, and 24 relative to the known positions of the pilot light sensors 26, 28, and 30. Finally, the parallax data from each of the sensors 16, 18, 26, 28, and 30 are ultimately fed to the coordinate computer 34, which determines the position of the illuminated spot 36 with respect to the predetermined reference frame by correlating the position of the illuminated spot 36 in relation to the scanner head 12 with the position of the scanner 12 in relation to the fixed pilot light sensors 26, 28, and 30, which are positioned in relation to the predetermined reference frame 80 at precisely predetermined locations at conveniently spaced distances from each other and from the object 38 and the hand-held scanner 12. If the computer can make these location or position calculations very fast, the operation can be performed over and over again in sequence as the scanner head 12 moves in relation to the object, thus resulting in effectively real time mensuration of the object as the scanner head 12 moves.

By using this two-stage measurement system, i.e., first measuring the location of the illuminated spot 36 in relation to the scanning head 12 at a particular instant in time, and then determining the position of the scanning head 12 in relation to the predetermined reference frame at that same instant in time, the optical mensuration apparatus 10 of the present invention dispenses with the need for high precision head positioning apparatus and the complex and expensive mechanical structure typically associated therewith. Further, the hand-held scanner, 12 is easily manipulated by the operator to direct the scanning beam 42 over complex, interior, or blind surface details, which would otherwise be difficult to scan, thus speeding the scanning operation.

Figure 2:
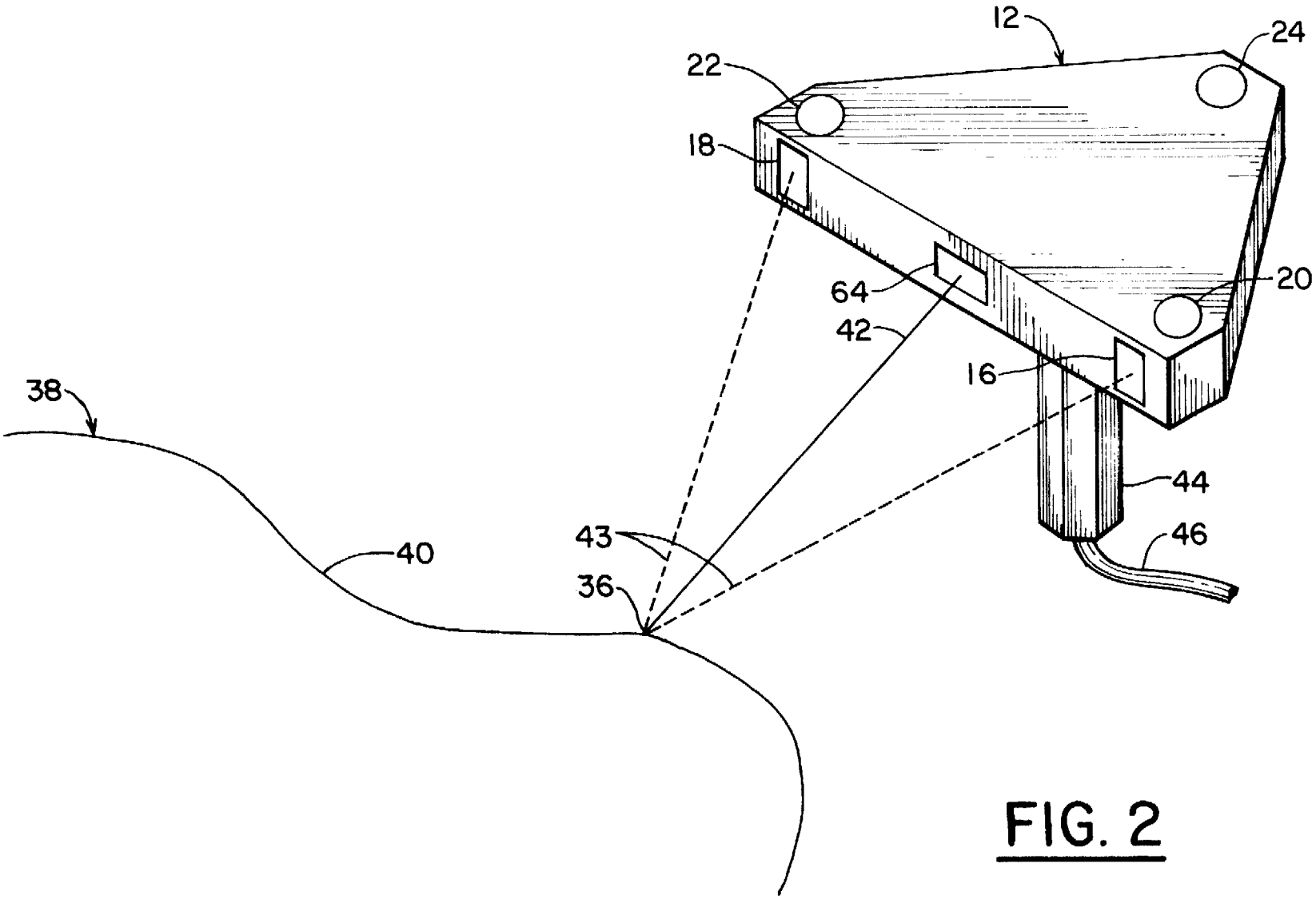
FIG. 2 is a perspective view of the hand held scanning head of the present invention, showing how it can be positioned to direct the scanning beam onto the surface of the object being scanned.
Figure 3:
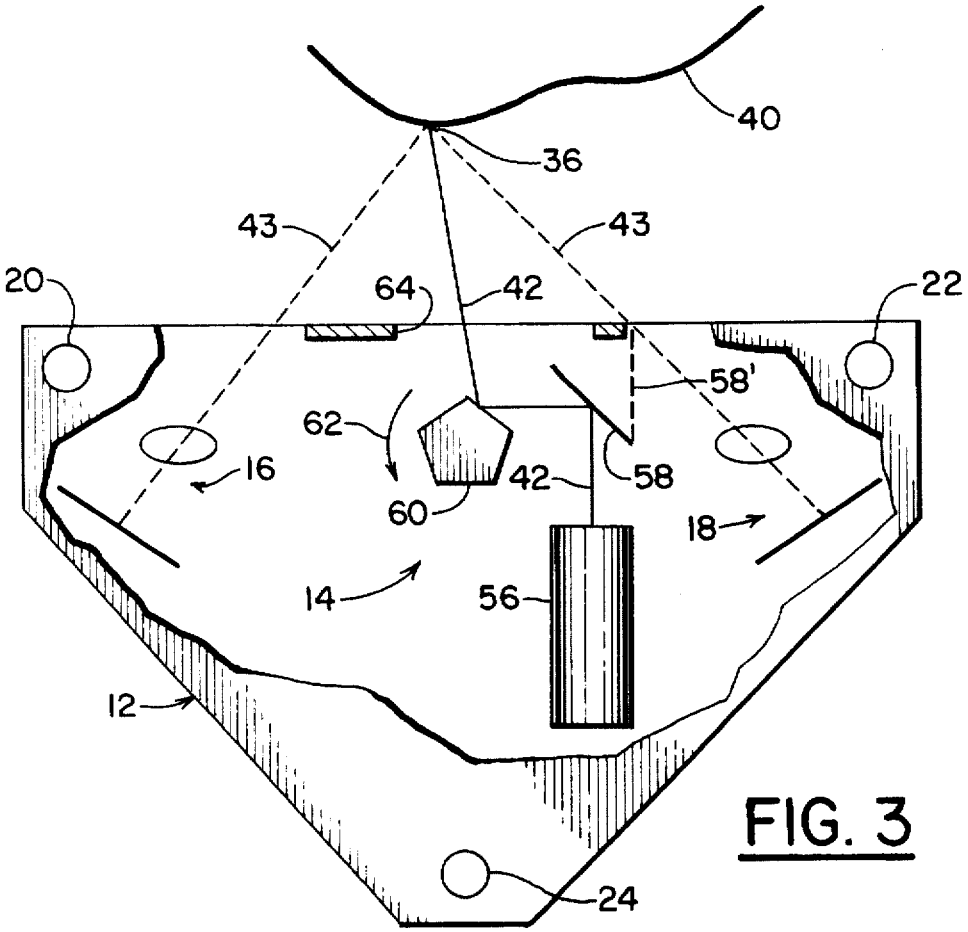
FIG. 3 is a plan view of the scanning head of the present invention with the top surface broken away to more clearly show the arrangement of the optical projecting apparatus and the spot detectors.
Figure 4:
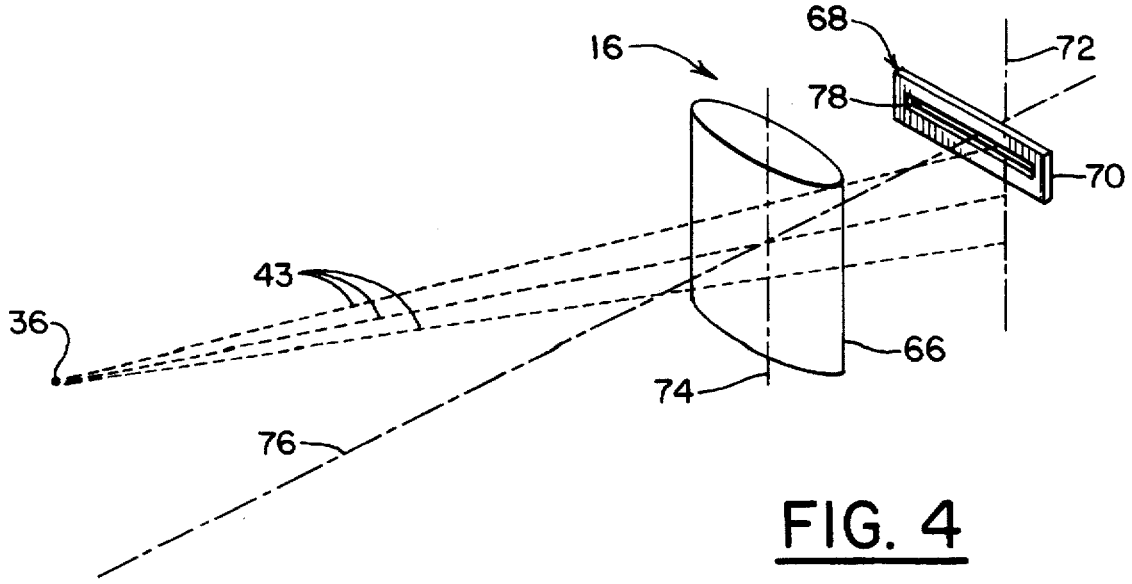
FIG. 4 is a schematic perspective representation of one of the one-dimensional photodetectors of the present invention.

The details of the optical mensuration apparatus 10 of the present invention are best understood by referring to FIGS. 2, 3, and 4 simultaneously. Essentially, the hand-held scanner head 12 houses the light beam projecting apparatus 14 (FIG. 3), the two one-dimensional spot sensors or detectors 16, 18, and the three pilot light emitters 20, 22, and 24. A handle 44 allows the scanner head 12 to be easily manipulated by the operator to guide the scanning beam 42 over the various shapes and hidden contours of the surface 40 of object 38.

In the preferred embodiment, the light beam projecting apparatus comprises a helium-neon (He-Ne) laser 56 to generate collimated scanning beam 42. Of course, other devices could be used to produce the spot-like scanning beam as would be readily apparent to persons having ordinary skill in the art. For example, laser 56 could be replaced by a light emitting diode (LED) and associated collimating lens. Other sources and lens combinations are possible so long as the apparatus is capable of projecting a small, well defined beam of light on the surface of the object. A planar mirror 58, which could be optionally pivotally mounted as shown in FIG. 3, directs beam 42 to a rotating many-faceted mirror 60, which directs, or scans beam 42 over the surface 40 in a single plane relative to the scanner 12 (i.e., the plane of the paper in FIG. 3). Of course, the number of sides of the rotating, many-faceted mirror 60 determines the angle through which scanning beam 42 sweeps. For example, the pentagonal mirror shown in FIG. 3 will sweep the beam through a 144-degree angle. More sides will sweep the beam through smaller angles. Moreover, other scanning paths are possible by using irregularly shaped mirrors or multiple rotating mirrors, and the present invention should not be regarded as limited by the particular scanning apparatus shown and described herein.

While the rotating mirror 60 can be rotated in either direction with equal effectiveness, the rotating mirror 60 in the preferred embodiment 10 is rotated in the direction indicated by arrow 62 by a simple, unsynchronized motor (not shown). As mentioned above, planar mirror 58 may be optionally pivotally mounted such that it can be swung out of the beam path to position 58' (shown in broken lines in FIG. 3) to inhibit the scanning action of the beam 42. With the mirror at position 58' the beam 42 will exit straight out aperture 64 in scanner 12 which can then be used as a point-type scanner or as a noncontact pointer for identifying some single point of interest on the surface 40 of object 38.

The details of the one-dimensional spot detectors 16, 18 are best understood by referring to FIG. 4. Actually, all of the one-dimensional sensors 16, 18, 26, 28, and 30 used in the preferred embodiment 10 of the present invention are identical to the one-dimensional spot detector 16 in every respect. Therefore, for the purpose of giving a detailed description of this embodiment, only the sensor 16 is shown and described in detail since the remaining sensors 18, 26, 28, and 30 have identical features.

Referring now to FIG. 4, the one-dimensional sensor 16 comprises a cylindrical lens 66 that has a longitudinal axis 74 which is orthogonal to the optical axis 76 of the sensor 16. A linear photodetector 68, such as a charge coupled device (CCD) with several thousand elements, or a similar device capable of linear light detection with an elongated aperture 78 is positioned in such a manner that optical axis 76 passes through aperture 78 and such that the long axis of aperture 78 is orthogonal to the plane containing the longitudinal axis 74 of lens 66. The incident light beam 43 reflected from illuminated spot 36 is then focused by the cylindrical lens 66 into a real image line 72 on the surface 70 of linear photodetector 68, which is a characteristic of this type of lens.

Figure 6:
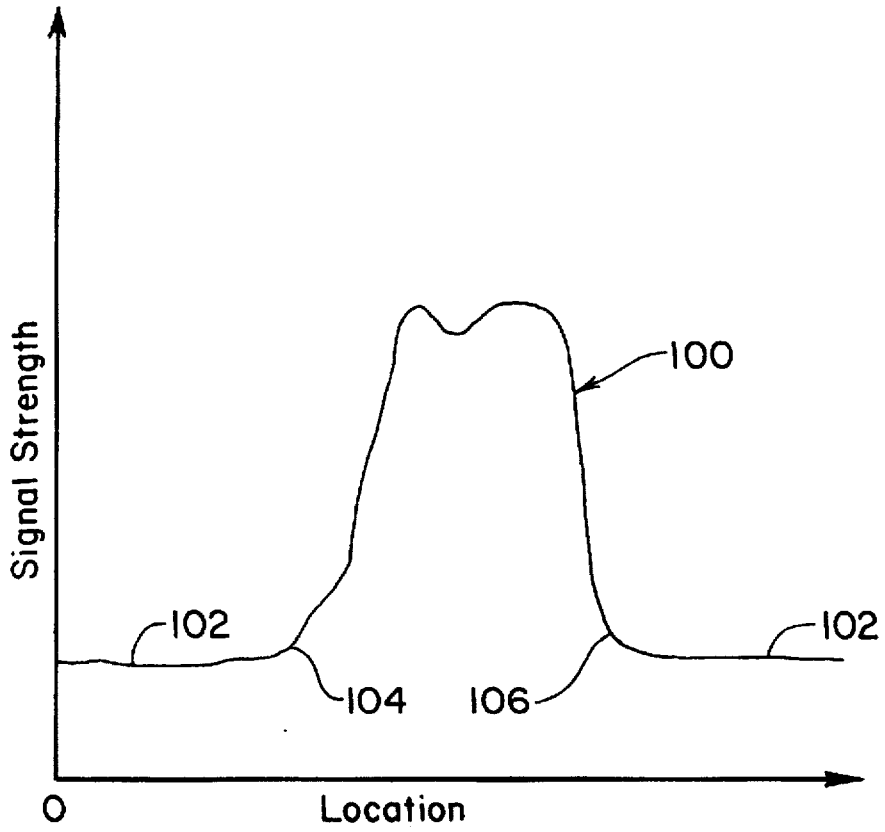
FIG. 6 is a graph of signal strength vs. location on the detector surface for a typical light detector used by the optical mensuration apparatus of the present invention.

The CCD detector 68 then generates a signal, such as the one shown in FIG. 6, that is related to the position of real image line 72 on the surface 70 of photodetector 68, thus characterizing the location of the image itself. That is, those elements of the detector 68 illuminated by the real image line 72 will generate a strong signal, while those not illuminated will generate a weak signal. Thus, a graph of signal strength vs. location on the surface of the CCD will resemble the signal peak curve 100 shown in FIG. 6. Note that the "zero" signal level 102 is never quite zero due to the effects of background light and other imperfections in the sensor. In any event, since the image of illuminated spot 36 is focused into line 72, only the horizontal displacement of spot 36 from optical axis 76 is measured by detector 68, hence the designation "one-dimensional detector."

Thus, a single one-dimensional detector 16 can only locate the plane on which spot 36 particular beam lies, but detector 16 cannot, by itself, determine the unique location or position in space on which point 36 is located. To precisely locate the location in space of point 36 would require three such detectors postitioned in spaced-apart relation to each other, since the intersection of three planes defines a point. However, if the plane containing the aperture 78 of detector 16 is in the same plane as the scanning beam 42, only two detectors are required to uniquely locate the position of spot 36. Therefore, in the preferred embodiment 10 of the present invention, the apertures 78 of the respective photodetectors 16, 18, lie in the same plane as the scanning beam 42, thereby allowing the exact point in space of illuminated spot 36 to be determined with only two detectors 16, 18.

The three pilot light emitters 20, 22, and 24 (FIGS. 1–3) can be high intensity light emitting diodes (LEDs), which are preferably time multiplexed or strobed by control unit 32 in a predetermined manner such that only one pilot light LED is "on" or emitting light at any one time. The light emitted from any one of these emitters 20, 22, and 24 is detected by each of the three pilot light detectors 26, 28, and 30, which then determine the position of that particular emitter in relation to the known positions of the detectors 26, 28, and 30 at the instant in time that it is strobed or illuminated. To locate the position of a particular illuminated one of emitters 20, 22, 24, the pilot light detectors 26, 28, and 30 are mounted so that their optical axes are not collinear. In the preferred embodiment, two pilot light detectors, such as detectors 26, 30 in FIG. 1, are situated such that their respective axes 74 (FIG. 4) are in parallel spaced-apart relation, with the third detector 28 situated between the first two, but with its axis 74 perpendicular to the first two. As described above, each of the detectors 26, 28, and 30 then determine a unique plane in which the given pilot emitter lies, the intersection of which defines the exact location of that illuminated emitter.

While this process of detecting the position of a given illuminated pilot emitter 20, 22, 24 can locate the exact position of the illuminated emitter, it cannot determine the particular orientation of the entire scanner head 12 in three-dimensions. To do so requires the detection of the locations of at least three spaced-apart emitters whose orientations with respect to one another are known. Therefore, the optical mensuration system 10 of the present invention determines the orientation of the scanning head 12 in three-dimensional space by using the three (3) pilot emitters 20, 22, and 24, whose relative positions on the scanning head 12 are fixed and known. Consequently, when each of the emitters 20, 22, and 24 are rapidly turned on in sequence, the sensors 26, 28, and 30 can detect the exact position of each emitter in turn, thus determine the exact location and orientation of the scanning head 12. Since only one of the pilot light emitters 20, 22, 24 is on at any one time, the detectors 26, 28, 30 locate the position of that particular illuminated pilot light only. If the strobe rate, that is, the frequency at which the emitters 20, 22, 24 are turned on and off in sequence, is fast enough, the detectors 26, 28, and 30 can, for all practical purposes, determine the position and orientation of the scanning head 12 at any instant in time.

Note that the detectors 26, 28, 30, need only distinguish which of the pilot light emitters 20, 22, 24 is "on" or illuminated at any one time. In the preferred embodiment 10 of the present invention, this function is accomplished by strobing or illuminating each of the emitters 20, 22, 24 in sequence. However, other methods could be used to allow the detectors 26, 28, 30 to distinguish the respective pilot light emitters 20, 22, 24 from one another. For example, different colors of light could be used in conjunction with detectors capable of distinguishing those particular colors or wavelengths of light. Alternatively, the respective pilot light emitters 20, 22, 24 could be modulated with a unique "tone" for each emitter. The control unit 32 or coordinate computer 34 could then be programmed to demodulate the tone, thus determine to which particular emitter 20, 22, or 24 the position signal belongs. Numerous other methods of distinguishing the pilot light emitters 20, 22, and 24 are possible and would be readily apparent to persons having ordinary skill in the art. Therefore, the present invention should not be regarded as limited to the particular strobing method shown and described herein.

Figure 5:
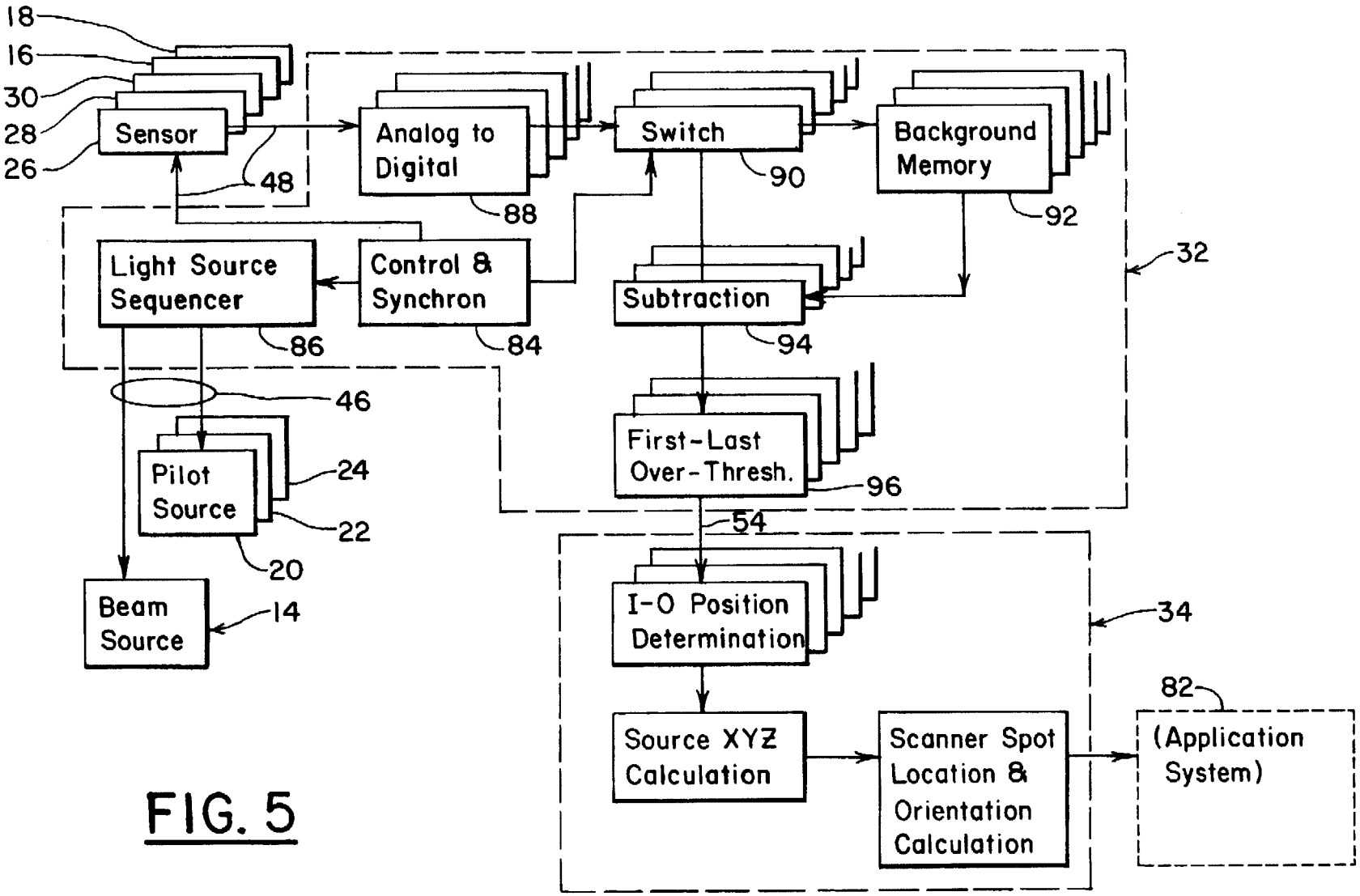
FIG. 5 is a schematic block diagram of the optical mensuration apparatus of the present invention showing in detail the functions and operations of the control unit and coordinate computer.

The details of the structure and operation of the control unit 32 are best seen in FIG. 5. Specifically, control unit 32 supplies power to the light beam projecting apparatus or source 14, the beam spot sensors 16, 18, the pilot light emitters or sources 20, 22, and 24, and the pilot light sensors 26, 28, and 30. The control and synchronization unit 84 and light source sequencer 86 time multiplexes or strobes the beam projecting apparatus 14 and the pilot lights 20, 22, and 24 individually, as described above, so that the position and orientation of the scanning head 12 can be determined from the signals received from pilot light sensors 26, 28 and 30. The angular data signals received from the pilot light sensors 26, 28, and 30 and from the spot sensors 16, 18, are converted by analog to digital converter 88. Actually, five analog to digital converters are used, as shown in FIG. 5, but only one is labeled and described herein for brevity, since the other four analog to digital converters are identical and are used to convert the signals from sensors 28 and 30 and 16 and 18, respectively.

The control and synchronization unit 84 also controls five switches, of which switch 90 is typical, which store all digital data received from the sensors 26, 28, and 30 and 16 and 18 when the pilot light emitters and scanning beam 42 are "off," and stores these data in background memory 92. Then, when the pilot light sources and scanning beam are illuminated in sequence by light source sequencer 86, the control and synchronization unit 84 changes the state of switch 90, which then redirects the data from the five sensors to the subtraction unit 94. Subtraction unit 94 substracts the "background" data from the illuminated data, thus resulting in a signal relatively free from background noise signal 102 (FIG. 6), since it has been subtracted from the signal.

Referring now to FIGS. 4 and 6 in conjunction with FIG. 5, the first-last over-threshold unit 96 computes the location of the real image line 72 on the CCD sensor 68 (FIG. 4) by measuring the locations of the edges 104, 106 of the signal blip 100 (FIG. 6) generated by the CCD sensor based on a predetermined threshold signal level. The first-last over-threshold unit 96 then averages the distance between the two edges to find the center of the signal peak, which is often dipped, as shown in FIG. 6. This particular method of determining the center of the signal peak is well known in the art and will not be described in further detail. Moreover, numerous other methods of determining the location of the signal peak are known in the art, and would be obvious to those having ordinary skill in the art. The particular method used would depend on the signal characteristics of the particular light sensor used, as well as the characteristics of the lens system used to focus the light onto the surface of the detector, as well as other parameters. Those practicing this invention with the various alternates described herein would have no trouble selecting a signal detection algorithm best suited to the particular characteristics of the sensors.

Finally, control unit 32 (FIG. 5) transmits the position data to the coordinate computer 34. That is, when the coordinate computer 34 is ready to compute the current location of the illuminated spot 36 on the object, the latest angular data from all sensors are provided for analyzation. If the spot sensors 16, 18, or the pilot light sensors 26, 28, and 30, generate data faster than the control unit 32 can process them, the angular data are simply discarded.

The details of the coordinate computer 34 are also best seen in FIG. 5. Essentially, the coordinate computer 34 calculates one-dimensional positions for each light source based on the location of the signal peak from each respective sensor. These one-dimensional positions are then used to calculate the three-dimensional spatial coordinates for the illuminated spot 36 and for the scanning head 12 in relation to the predetermined coordinate system 80, by coordinate transformation methods which are well-known in the art. The output from the coordinate computer 34 can be in any form desired by the operator or required by the application system 80, such as XYZ coordinate triples based upon some predetermined stationary rectangular coordinate system.

The operation of the optical mensuration apparatus of the present invention is as follows. Upon illumination of a spot 36 on the surface 40 of object 38, the two spot sensors 16, 18 inside the scanner head 12 sense the angular position of the illuminated spot 36 at a given instant in time. The signals from these spot sensors 16, 18, are directed to the control unit 32 via data line 46. Next, the pilot light detectors 26, 28, and 30 are used to sense the individual positions of the three pilot light emitters 20, 22, 24 in sequence as described above. That is, each pilot light detector 26, 28, 30, measures the angle of rays from each of three pilot light emitters 20, 22, 24, mounted on the scanner 12. The angular data from each of these sensors 26, 28, and 30 are also directed to control unit 32 via data lines 48, 50, and 52.

As described above, the control unit 32 converts the angular data from each of the sensors 16, 18, 26, 28, and 30, which is in analog form, to digital data and tags these data with information identifying their respective sources. These converted digital data are then processed by removing the background noise and by using known signal detection methods to determine the center of the signal peak, thus the location of the image line 72 on the detector 68. These position locations of the centers of the respective signal peaks from each detector 16, 18, 26, 28, and 30 are then directed to coordinate computer 34 via data line 54, which then computes the current location of the illuminated spot 36 with respect to the predetermined coordinate system 80. Sequential calculations and beam spot position determination can be made as fast as the computer can do so, thus many such points on the surface of the object can be determined as they are scanned almost on a real time basis. These position data can be stored in computer memory, recalled, and correlated together to produce an image of the object in precise reproduction detail, or various points or other features on the object can be mensurated or used in any manner desired.

This completes the detailed description of the method and apparatus of the optical mensuration apparatus 10 of the present invention. While some of the obvious and numerous modifications and equivalents have been described herein, still other modifications and changes will readily occur to those skilled in the art. For instance, the preferred embodiment uses visible light since human operators can readily observe if the light sources are operative or whether they are causing troublesome reflections. Clearly, other wavelengths of electromagnetic radiation could be used without departing from the spirit and scope of this invention. Further, it would be possible to include circuitry in the detectors which would subtract out the ambient light, thus improve the detection efficiency of the invention. Other modifications to the detector optics and lenses are possible which would alter the image characteristics on the detectors. For example, cylindrical lenses could be used which have been longitudinally curved along an arc with a radius equal to the focal length of the lens. Similarly, the surfaces of the photodetectors could also be curved, thus allowing the images of distant light sources to remain in sharp focus regardless of their positions. Various measurements of the detector outputs are also possible. For example, the angle of peak intensity, the intensity-weighted average, or the average of the minimum and maximum angles where the intensity is over some predetermined threshold value could be used. Finally, numerous enhancements of the digital data are possible by programming the coordinate computer to make the appropriate enhancements, as would be obvious to those persons having ordinary skill in the art.

The foregoing is considered illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to as falling within the scope of the invention as defined by the claims which follow.

The embodiments of the invention in which an exclusive property or privilege is claimed are defined as follows:

1. Optical mensuration apparatus for mapping and recording the locations of points on a surface of a three dimensional object comprising:

[a mounting structure, and] *an* object positioned in [immovable relation to said mounting structure, and] a three dimensional coordinate system [defined in fixed relation to said mounting structure];

[scanning means] *a scanner* for projecting a scanning beam onto [the] *a* surface of [the] *an* object to illuminate a plurality of spots on the surface of the object;

said [scanning means] *scanner* being hand holdable and freely moveable by hand in relation to [both said mounting structure and] said object and not connected mechanically or structurally to [either said mounting structure and] said object;

*a* spot detector [means] mounted to said [scanning means] *scanner* for detecting the [positions] *locations* of the illuminated spots on the surface of the object in relation to said [scanning means] *scanner*;

*a* position [detecting means mounted on said mounting structure and] *detector* remotely located from both said object and said [scanning means for detecting the position of said scanning means] *scanner* in *known* relation to [the] *said* coordinate system, *which position detector is adapted to determine the position of said scanner in relation to said three dimensional coordinate system*; [and computing means] *a computer* connected to said [scanning means] *scanner* and to said position [detecting means] *detector* for determining [and recording] the [positions] *locations* of said illuminated spots on the surface of the object in relation to the coordinate system by correlating the [positions] *locations* of said illuminated spots in relation to said [scanning means] *scanner* with [the respective] positions of said [scanning means] *scanner* in relation to said coordinate system when [each] *a* respective spot is illuminated.

2. The optical mensuration apparatus of claim 1, wherein said spot detector [means] comprises a plurality of one dimensional spot [sensing means] *sensors* in spaced apart relation for sensing the [position] *locations* of the illuminated spots on the surface of the object.

3. The optical mensuration apparatus of claim 2, wherein each of said one dimensional spot [sensing means] *sensors* comprises:

a linear photodetector; and a lens positioned between said linear photodetector and said illuminated spot on the object for focusing light from said illuminated spot onto said linear photodetector.

4. The optical mensuration apparatus of claim 3, wherein said position [detecting means] *detector* comprises:

a plurality of pilot light [source means] *sources* mounted on said [scanning means] *scanner* for projecting a plurality of pilot light rays; and a plurality of one-dimensional pilot light [sensing means] *sensors* in spaced apart relation remotely located from said [scanning means] *position detector* for sensing the [positions] *locations* of each of said plurality of pilot light [source means] *sources*.

5. The optical mensuration apparatus of claim 4, wherein each said one-dimensional pilot light [sensing means] *sensors* comprises:

a linear photodetector; and a lens positioned between said linear photodetector and said plurality of pilot light [source means] *sources* for focusing light from said plurality of pilot light [source means] *sources* onto said linear photodetector.

6. The optical mensuration apparatus of claim 5, wherein each of said plurality of light [source means] *sources* is strobed off and on in a predetermined manner.

7. The optical mensuration apparatus of claim 5, wherein said [scanning means] *scanner* comprises:

*at least one* light source [means] for producing said scanning beam; and

*a corresponding number of* scanning beam [direction means] *directors* for directing said scanning beam over the surface of the object.

8. The optical mensuration apparatus of claim 7, wherein said light source [means] for producing said scanning beam is a laser.

9. The optical mensuration apparatus of claim 7, wherein said scanning beam [direction means] *director* is a rotating mirror having at least three sides.

10. The optical mensuration apparatus of claim 9, wherein each said lens of each said one-dimensional spot [sensing means] *sensor* is a cylindrical lens.

11. The optical mensuration apparatus of claim 9, wherein each said lens of each said one-dimensional pilot light [sensing means] *sensor* is a cylindrical lens.

12. A method of determining and mapping the locations of surface points on an object in relation to a [mounting structure] *three dimensional coordinate system*, comprising the steps of:

defining a three dimensional coordinate system [in fixed relation to said mounting structure];

positioning said object in a fixed spatial relation to said [mounting structure] *coordinate system*;

projecting a [scanning] *scannable illuminating* beam from a beam projector, [mounted on a hand holdable and freely moveable scanning device] that is not connected mechanically or structurally to [either said mounting structure or] the object, [and moving the scanning device by hand in relation to said object] in such manner as to illuminate a [plurality of spots on the] *a sufficient portion of a* surface of the object *to map said surface*;

*scanning said surface with a hand holdable and freely moveable scanner to detect a sufficient portion of said projected beam illuminations to map said illuminated surface portion*;

detecting the [positions] *locations* of the respectively illuminated [spots on] *portions of* the surface of the object in relation to the respective positions of the [scanning device] *scanner* when each respective [spot] *portion of the surface* is illuminated;

projecting a plurality of pilot light rays from a plurality of pilot light sources positioned in fixed spatial relation to each other on said [scanning device] *scanner substantially* simultaneously with the steps of projecting said [scanning] *illuminating* beam and detecting the [positions] *locations* of the illuminated [spots] *surface portions*;

detecting the plurality of pilot rays with a plurality of detectors mounted [on said mounting structure in fixed] *in known* relation to said coordinate system and in [fixed] *known*, spaced apart relation to each other *substantially* simultaneously with the step of detecting the [positions] *locations* of said illuminated [spots] *surface portions* on said object in relation to said [scanning device] *scanner* to determine the [positions] *locations* of the plurality of pilot light sources and said [scanning device] *scanner* in relation to the coordinate system; and computing the [positions] *locations* of the illuminated [spots on] *portions of* the surface of the object in relation to the coordinate system by correlating the [positions] *locations* of said illuminated [spots] *surface portions* in relation to the [scanning device] *scanner* with the [position] *locations* of the [scanning device] *scanner* in relation to said coordinate system.

*13. Optical mensuration apparatus for mapping and recording the locations of points on a surface of a three dimensional object as claimed in claim 1 further comprising a mounting structure, fixedly positioned in said three dimensional coordinate system, to which said object is immovably related, and wherein said position detector is mounted on said mounting structure.*

*14. An optical system as claimed in claim 13 further comprising:*

*multiple energy emitters disposed on said spot detector;*

*emitted energy detectors disposed in known relationship to said three dimensional coordinate system sufficient to detect energy emitted by said energy emitters; and*

*a computer operatively associated with said energy detectors adapted to calculate the position and orientation of said light detector in said three dimensional coordinate system.*

*15. An optical system for determining locations of a plurality of points on a portion of a surface of a three dimensional object, in relation to a three dimensional coordinate system in which said object resides, wherein the number of points on said surface portion is sufficient to map said surface portion, said system comprising:*

*at least one three dimensional object having at least one surface positioned in a three dimensional coordinate system;*

*a beam projector unconnected mechanically or structurally to said object, and freely moveable in relation to said object;*

*at least one scannable beam adapted to be projected from said projector onto a surface of said object and to thereby illuminate said plurality of points on said surface portion;*

*a scanner comprising at least one light detector, unconnected mechanically or structurally to said object, and freely moveable in relation to said object, and adapted to detect locations of said illuminated points on said surface of said object in said three dimensional coordinate system in relation to said spot detector;*

*means to maintain said object in a substantially stationary condition during said illumination and detection of at least three of said plurality of spots sufficient in number to map said surface portion of said object;*

*at least one light detector locator disposed in known position in said three dimensional coordinate system, for optically detecting the position and orientation of said light detector in relation to said three dimensional coordinate system; and*

*a computer connected to said light detector and to said detector locator for correlating respectively the locations of said illuminated portions of said surface of said object in relation to said light detector and the location of said light detector in relation to said three dimensional coordinate system;*

*whereby indirectly determining the locations of each of said illuminated surface portions with respect to said three dimensional coordinate system, and therefore mapping said portion of said surface of said object.*

*16. An optical system as claimed in claim 15 wherein said light detector is located together with said illuminating beam projector.*

*17. An optical system as claimed in claim 15 wherein said light detector locator is located together with said object.*

*18. An optical system as claimed in claim 15 wherein said scanner is hand held and is moved by hand.*

*19. An optical system as claimed in claim 15 further comprising said locator being adapted to locate said light detector at substantially the same time as the locations of each of said illuminated surface portions are being detected by said light detector.*

*20. An optical system as claimed in claim 15 wherein said object is in a fixed position in said three dimensional coordinate system.*

*21. An optical system as claimed in claim 20 wherein said object is attached to a mounting structure which is in fixed spatial relationship to said three dimensional coordinate system, wherein said scanner has said light detector affixed thereto, and wherein said light detector locator in fixed relationship to said mounting structure.*

*22. A method of mapping at least a portion of a surface on an object, which object is in a known position and orientation in a three dimensional coordinate system, comprising:*

*disposing an object, comprising at least one surface, in a known position and orientation in a three dimensional coordinate system;*

*disposing a hand holdable scanner in said coordinate system, unconnected mechanically or structurally to said object and freely moveable within said three dimensional coordinate system, so positioned that it can scan said surface;*

*projecting a plurality of spots onto said surface portion;*

*detecting the locations on said surface portion, in relation to a spot detector, of a sufficient number of spots to map at least said portion of the surface;*

*at substantially the same time as the locations of the respective spots are being determined, determining the location of said spot detector in said coordinate system;*

*correlating the locations of said respective spots with the position and orientation of said spot detector; thereby indirectly determining the locations of said illuminated spots in said three dimensional coordinate system; and*

*mapping said surface.*

* * * * *